US006703515B2

(12) United States Patent
Saud et al.

(10) Patent No.: US 6,703,515 B2
(45) Date of Patent: Mar. 9, 2004

(54) CHIRAL DERIVATIVES OF HIBISCUS ACID BEARING LACTONE RING MOIETY, PROCESS FOR PREPARING THE SAME AND A CONVENIENT METHOD FOR THE LARGE-SCALE ISOLATION OF HIBISCUS ACID

(75) Inventors: Ibrahim Ibnu Saud, Kerala (IN); Chitra Gopinath, Kerala (IN); Beena Thomas, Kerala (IN)

(73) Assignee: Department of Science and Technology, Technology Bhavan, New Delhi (IN)

( * ) Notice: Subject to any disclaimer, the term of this patent is extended or adjusted under 35 U.S.C. 154(b) by 0 days.

(21) Appl. No.: 09/946,817

(22) Filed: Sep. 5, 2001

(65) Prior Publication Data

US 2003/0088110 A1 May 8, 2003

(30) Foreign Application Priority Data

Oct. 3, 2000 (IN) ..................... 884/DEL/2000

(51) Int. Cl.⁷ .......................... C07D 307/02
(52) U.S. Cl. ..................... 549/295; 549/313
(58) Field of Search ................. 549/313, 295

(56) References Cited

U.S. PATENT DOCUMENTS

| | | | |
|---|---|---|---|
| 3,764,692 A | 10/1973 | Lowenstein .................. | 424/279 |
| 4,005,086 A | 1/1977 | Guthrie et al. ............ | 260/247.2 |
| 4,006,166 A | 2/1977 | Guthrie et al. ............ | 260/343.6 |
| 4,007,208 A | 2/1977 | Guthrie et al. ............ | 260/343.6 |
| 5,536,516 A | 7/1996 | Moffett et al. .............. | 426/271 |
| 6,127,553 A | 10/2000 | Ibnusaud et al. ........... | 549/313 |
| 6,147,228 A | 11/2000 | Ibnusaud et al. ........... | 549/318 |
| 6,489,492 B2 | 12/2002 | Saud et al. .................. | 549/318 |
| 6,489,493 B2 | 12/2002 | Saud et al. .................. | 549/453 |
| 2002/0042528 A1 | 4/2002 | Saud et al. .................. | 549/454 |

OTHER PUBLICATIONS

Chemical Abstracts, vol. 85, 1976. Page 113, Section 85: 41531x.
Chemical Abstracts, vol. 86, 1977. Page 340, Section 86: 186629r.
Chemical Abstracts, vol. 87, 1977. Page 227, Section 87: 195626k.
Chemical Abstracts, vol. 96, 1982. Page 236, Sections 96: 30421n and 96: 30422p.
Boll, et al. "Naturally Occurring Lactones and Lactames, III. The Absolute Configuration of Hydroxycitric Acid Lactones: Hibiscus Acid and Garcinia Acid," Acta Chemica Scandinavia, vol. 23, No. 1, 1969. Pp. 286–293.
Cardellach et al. "Studies on Structurally Simple – α,β–Butenolides—I, New Synthesis of Racemic γ–Hydroxymethyl–α,β–Butenolide and Derivatives," Tetrahedron, vol. 38, No. 15, 1982. Pp. 2377–2394.

Chen et al. "Use of D–Ribonolactone in Organic Synthesis. 2. Scope and Utility," J. Org. Chem, vol. 49, No. 14, 1984. Pp. 2168–2174.
Doolittle et al. "(S)–Tetrahydro–5–oxo–2–furancarboxylic Acid: A Chiral Derivatizing Reagent for Asymmetric Alcohols," J. Org. Chem., vol. 49, No. 26, 1984. Pp. 5041–5050.
Drioli et al. "Synthesis of (+)– and (–)–Phaseolinic Acid by Combination of Enzymatic Hydrolysis and Chemical Transformations with Revision of the Absolute Configuration of the Natural Product," J. Org. Chem., vol. 63, No. 7, 1998. Pp. 2385–2388.
Herrmann et al. "Method for Alkylating Lactones," J.C.S. Chem. Comm., No. 962, 1973. Pp. 711–712.
Koch et al. "Enantioselective Preparation of β–Alkyl–γ–butyrolactones from Functionalized Ketene Dithioacetals," J. Org. Chem., vol. 58, No. 10, 1993. Pp. 2725–2737.
Kunesch et al. "Structure and Synthesis of the Wing Gland Pheromone of the Male African Sugar–Cane Borer: *Eldana saccharina* (WLK.)," Tetrahedron Letters, vol. 22, No. 52, 1981. Pp. 5271–5274.
Louwrier et al. "Studies Towards the Synthesis of (+)–Ptilomycalin A; Stereoselective N–Acyliminium Ion Coupling Reactions to Enantiopure C–2 Substituted Lactams," Tetrahedron Letters, vol. 52, No. 7, 1996. Pp. 2603–2628.
Martins et al. "Darstellung, physiologioches Verhalten und Bedentung der (+)–Oxycitronensaure und ihrer Isomeren," Physiological Chem., vol. 269, 1941, Pp. 33–40.
Moret et al. "A Diastereoselective Synthesis of Both Quercus Lactone Isomers Employing Allyl–Type Organometallics as Key Intermediates," Tetrahedron Letters, vol. 25, No. 40, 1984. Pp. 4491–4494.
Mori, K. "Synthesis of Optically Active Forms of Sulcatol, The Aggregation Pheromone in the Scolytid Bettle, *Gnathotrichus sulcatus*," Tetrahedron, vol. 31, No. 24. Pp. 3011–3012.

(List continued on next page.)

*Primary Examiner*—Amelia Owens
(74) *Attorney, Agent, or Firm*—Sidley Austin Brown & Wood LLP

(57) ABSTRACT

The present invention relates to a novel chiral compound of Hibiscus acid bearing lactone moiety of formula I,

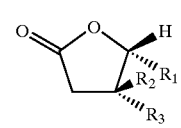

Wherein:
$R_1=R_2=$alkali salt of carboxylic acid or acid chloride or lower esters or the N-substituted cyclic imides.
$R_3=$hydroxyl or protected hydroxyl group and a process for preparing the same.

33 Claims, No Drawings

OTHER PUBLICATIONS

Ortuno et al. "Reactions of Some D–Ribonolactone Derivatives With Alkyl Cuprates Synthesis of (+)–Eldanolide and (+)–trans–Cognac Lactone," Tetrahedron, vol. 43, No. 19, 1987. Pp. 4497–4506.

Pfenninger, A. "Asymmetric Epoxidation of Allylic Alcohols: The Sharpless Epoxidation," Synthesis, 1986. Pp. 89–116.

Ravid et al. "Synthesis of the Enantiomers of 4–Substituted γ–Lactones with Known Absolute Configuration," Tetrahedron, vol. 34, No. 10, 1978. Pp. 1449–1452.

Vigneron et al. "Absolute Configuration of Eldanolide, the Wing Glad Pheromone of the Male African Sugar Cane Borer, *Eldana saccharina* (Wlk.) Synthesis of its (+) and (−) Enantiomers," Tetrahedron Letters, vol. 23, No. 48, 1982. Pp. 4987–5096.

Yamanoi et al. "Preparation of Enantiopure 2,2,5,5–Tetramethyl–3,4–hexanediol and its Use in Catalytic Enantioselective Oxidation of Sulfides to Sulfoxides," J. Org. Chem., vol. 62, No. 24, 1997. Pp. 8560–8564.

Ibnusaud, I. et al. "Chiral γ–butyrolactones related to optically active 2–hydroxycitric acids." Tetrahedron vol. 58 (2002) pp. 4887–4892.

Jena, B.S. et al. "Chemistry and Biochemistry of (−)–Hydroxycitric Acid from Garcinia." Journal of Agricultural and Food Chemistry vol. 50 (2002) pp. 10–22.

Narasaka, K. et al. "Use of 1,3–Oxazolidin–2–one Derivatives of 3–Borylpropenoic Acids as β–Hydroxy Acrylic Acid Equivalents in the Asymmetric Diels–Alder Reaction Catalyzed by a Chiral Titanium Regent." Tetrahedron vol. 48, No. 27 (1992) pp. 5743–5754.

Seebach, D. et al. "TADDOLs, Their Derivatives and TADDOL Analogues: Versatile Chiral Auxiliaries." Agnew Chem. Int. Ed. vol. 40 (2001) pp. 92–138.

CHIRAL DERIVATIVES OF HIBISCUS ACID BEARING LACTONE RING MOIETY, PROCESS FOR PREPARING THE SAME AND A CONVENIENT METHOD FOR THE LARGE-SCALE ISOLATION OF HIBISCUS ACID

FIELD OF THE INVENTION

The invention relates to novel chiral derivatives of Hibiscus acid bearing lactone ring moiety and the process for preparing the same.

BACKGROUND OF THE INVENTION

Hibiscus acid [(+)-Hydroxycitric acid lactone or (2S,3R)-Tetrahydro-3-hydroxy-5-oxo-2,3-furandicarboxylic acid] can be isolated from the leaves/fruit calyxes of *Hibiscus sabdariffa* or from the leaves of *Hibiscus furcatus*, and *Hibiscus cannabinus*. Garcinia acid [(−)-Hydroxycitric acid lactone or (2S,3S)-Tetrahydro-3-hydroxy-5-oxo-2,3-furandicarboxylic acid,], a diastereomer of Hibiscus acid is widely used as an important ingredient in many pharmaceutical formulations[1-10].

The non-availability of Hibiscus acid in the market, in the optically pure form, has resulted in the limited use of Hibiscus acid or its derivatives in the broad area of organic synthesis and pharmaceutical front. This is due to the lack of any commercially viable large-scale manufacturing process. In U.S. patent application Ser. No. 09/365,300 an economic, commercially viable, cost effective process for the large-scale isolation of Hibiscus acid has been described[11].

Also during the past two decades there has been a great deal of interest to find cheap and potential chiral molecules from chiral pool to accomplish synthetic pathways with a high degree of asymmetric induction[12-25].

Added to this, substituted γ-butyrolactones are known to be potent antagonists or agonists depending upon the substitution pattern of the γ-aminobutyric acid receptor, the major inhibitory neurotransmitter in the mammalian central nervous system[26].

The known methods for obtaining diversity functionalised chiral γ-lactones are either by the cyclisation of acyclic starting materials such as the sterioselective iodolactonisation of unsaturated 3-hydroxy acids[27] or from sugars such as D-ribofuranose or D-glucosamine or carbohydrates such as D-ribose, D-glucose etc[28]. These chemical modifications involving carbohydrates require tedious protocols.

Existing Methods:

a. The method reported by Per. M. Boll, Else Sorensen and Eric Balieu[29] for the isolation of Hibiscus acid is from the calyxes of the fruits of *Hibiscus sabdariffa*. In this method dried, ground fruit calyxes of *Hibiscus sabdariffia* is extracted at room temperature for 68 hours several times with methanol containing 1.5% hydrogen chloride. To the pooled methanol extracts, ether is added and the coloring matter is deposited as a dark red syrupy mass. The ether layer is collected and syrup is dissolved in methanolic hydrogen chloride (1%) and again precipitated by the addition of ether. The pooled ether extracts is evaporated and the residue is dissolved in methanol. Upon cooling colorless crystals is obtained and the same is recrystallised from propanol and which was later hydrolysed to get Hibiscus acid.

b. Another method for the laboratory-scale production of Hibiscus acid described by C. Martius and R. Maue[30], is purely a synthetic one. In this method Hibiscus acid is prepared from a number of chemical constituents and not from any natural source.

c. The method described by this author and co-workers is a general method for the isolation of Hibiscus acid in the optically pure crystalline form from the fresh or dried leaves and/or calyxes of *Hibiscus sabdariffa* and leaves of *Hibiscus furcatus* or *Hibiscus cannabinus* employ mostly organic solvents. The main extraction is done with acidic methanol, followed out by the removal of organic impurities by adding water. The resulting filtrate was further extracted with organic solvents to get crude Hibiscus acid, which was later purified by esterification followed by hydrolysis.

The Drawbacks of the Existing Method "a" are:

1. The method fails to get pure Ia when leaves of the plants is used and is applicable only in the case of the fruit calyxes of *Hibiscus sabdariffa*.
2. *Hibiscus sabdariffa* is a seasonal flowering plant and hence the calyxes is not available at any given time.
3. Large quantities of expensive solvent ether is required for the process.
4. Crystallisation was effected only on prolonged (2 months) storage over drierite, in a desiccater.

Method "b" describes the synthesis of formula Ia from chemical constituents and is not economically viable.

None of the existing methods (a&b) describes the complete characterization and degree of purity of the compound.

Method "c" describes basically the extraction with undesirable methanol and expensive diethyl ether as solvents.

The object of the present invention therefore is to prepare chial derivatives bearing lactone ring moiety and to provide a new method obviating the drawbacks of the existing methods.

To achieve the objectives, this invention provides novel chiral derivatives of Hibiscus acid bearing lactone ring moiety of formula I

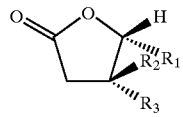

Formula I

Wherein:

$R_1=R_2=$alkali salt of carboxylic acid or acid chloride or lower esters or the N-substituted cyclic imides.

$R_3=$hydroxyl or protected hydroxyl group

In the above formula I $R_1$ and $R_2$ is selected from

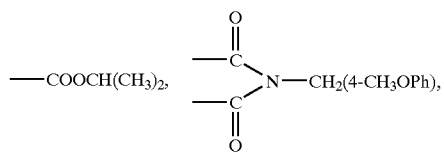

—COONa, —COCl, —COOCH$_2$C$_6$H$_5$, —COOC$_2$H$_5$, —COOCH(CH$_3$)$_2$, —CH$_2$(4-CH$_3$OPh),

-continued

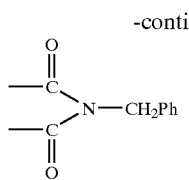

R$_2$ is —OH or protected hydroxyl group to form various chiral derivatives of Hibiscus acid bearing lactone ring moiety.

Chiral Derivatives of Hibiscus Acid Bearing Lactone Ring Moiety:

| | | |
|---|---|---|
| Ib- | R$_1$ = R$_2$ = —COONa, | R$_3$ = —OH |
| Ic- | R$_1$ = R$_2$ = —COCl, | R$_3$ = —OH |
| Id- | R$_1$ = R$_2$ = —COOCH$_3$, | R$_3$ = —OCH$_2$SCH$_3$ |
| Ie- | R$_1$ = R$_2$ = —COOCH$_2$C$_6$H$_5$, | R$_3$ = —OH |
| Ig- | R$_1$ = R$_2$ = —COOC$_2$H$_5$, | R$_3$ = —OH |
| Ih- | R$_1$ = R$_2$ = —COOCH(CH$_3$)$_2$, | R$_3$ = —OH |

Ij-

R$_1$,R$_2$ = [structure: —C(=O)—N(CH$_2$(4-CH$_3$OPh))—C(=O)—]    R$_3$ = —OCOCH$_3$ Ik- R$_1$,R$_2$ = [structure: —C(=O)—N(CH$_2$Ph)—C(=O)—]    R$_3$ = —OCOCH$_3$ Summary of the Chiral Derivatives of Hibiscus Acid Bearing Lactone Ring Moiety is Given Below in Scheme I:

SCHEME I

Formula I

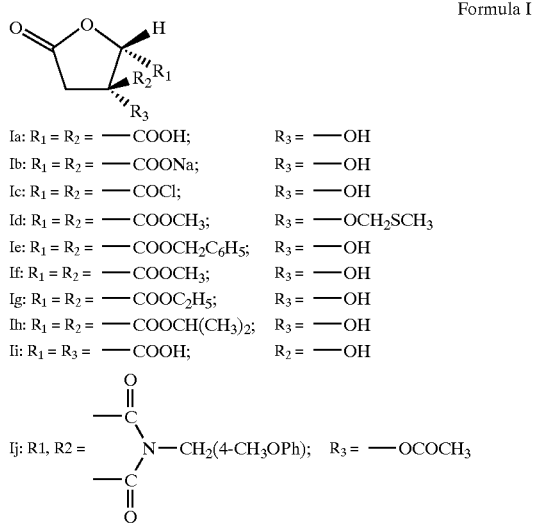

| | | |
|---|---|---|
| Ia: R$_1$ = R$_2$ = —COOH; | R$_3$ = —OH | |
| Ib: R$_1$ = R$_2$ = —COONa; | R$_3$ = —OH | |
| Ic: R$_1$ = R$_2$ = —COCl; | R$_3$ = —OH | |
| Id: R$_1$ = R$_2$ = —COOCH$_3$; | R$_3$ = —OCH$_2$SCH$_3$ | |
| Ie: R$_1$ = R$_2$ = —COOCH$_2$C$_6$H$_5$; | R$_3$ = —OH | |
| If: R$_1$ = R$_2$ = —COOCH$_3$; | R$_3$ = —OH | |
| Ig: R$_1$ = R$_2$ = —COOC$_2$H$_5$; | R$_3$ = —OH | |
| Ih: R$_1$ = R$_2$ = —COOCH(CH$_3$)$_2$; | R$_3$ = —OH | |
| Ii: R$_1$ = R$_3$ = —COOH; | R$_2$ = —OH | |

Ij: R1, R2 = [structure: —C(=O)—N(CH$_2$(4-CH$_3$OPh))—C(=O)—];   R$_3$ = —OCOCH$_3$ -continued

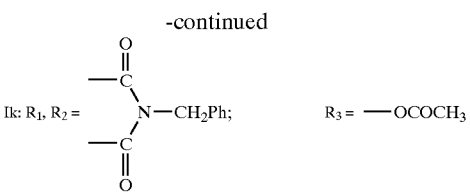

Ik: R$_1$, R$_2$ = [structure with N—CH$_2$Ph];   R$_3$ = —OCOCH$_3$

Compound of formula Ib is Disodium (2S,3R)-tetrahydro-3-hydroxy-5-oxo-2,3-furandicarboxylate Compound of formula Ic is (2S,3R)-Tetrahydro-3-hydroxy-5-oxo-2,3-furandicarbonylchloride Compound of formula Id is Dimethyl (2S,3R)-tetrahydro-3-oxo-[(methylthio)methoxy]-5-oxo-2,3-furandicarboxylate Compound of formula Ie is (phenylmethyl)(2S,3R)-tetrahydro-3-hydroxy-5-oxo-2,3 furandicarboxylate Compound of formula Ig is Diethyl (2S,3R)-tetrahydro-3-hydroxy-5-oxo-2,3-furandicarboxylate.

Compound of formula Ih is s Diisopropyl (2S,3R)-tetrahydro-3-hydroxy-5-oxo-2,3-furandicarboxylate.

Compound of formula Ij is (3aR,6aS)-3a-(acetyloxy) dihydro-5-(4-methoxy-phenyl methyl)-6H-furo[2,3-c] pyrrole-2,4,6(3H,4H)-trione The present invention further provides a process of isolation of compound of Formula Ia, comprising:

extracting the Calyxes/leaves of *Hibiscus sabdariffa*, leaves of *Hibiscus furcatus* and *Hibiscus cannabinus* using water (X), washing the extract (X) with organic solvent to remove impurities, concentrating the aqueous layer, adding an organic solvent to remove insoluble impurities, evaporating the organic layer, adding aqueous alkali to the concentrate to yield the alkali salt, purifying the alkali salt by the addition of alcohol, readjusting the pH by the addition of mineral acid, concentrating and extracting the solution with organic solvents, further concentrating the solution to get a syrup, extracting the said syrup with solvents, concentrating the obtained solution to get pure Ia in crystalline form.

The organic solvent used for washing is hexane.

The organic solvent used for removing impurities is selected from methanol or acetone.

The invention further includes a process for preparing the chiral derivative of Hibiscus acid of formula Ib comprising:

treating the aqueous solution of Ia with aqueous solution of alkali till the pH of the solution is neutral, evaporating the resultant solution to dryness, washing the residue with water miscible organic solvent, drying the product Ib under vacuum.

The said alkali is sodium bicarbonate.

The invention further includes a process for preparing the chiral derivative of formula Ic comprising:

adding an organic halide to a suspension of Ib in organic solvent, stirring the mixture for 1–4 hours, filtering the said mixture, evaporating the said solution to get Ic as a hygroscopic solid.

The said organic solvent is ether.

The said organic halide is thionyl chloride.

The invention also includes a process for preparing the chiral derivative of Formula Id comprising:

adding DMSO, an organic acid and an anhydride to If, allowing the mixture to stand for 34 days, adding the reaction mixture to cold saturated aqueous solution of alkali, stirring the mixture for 14 hours, extracting the resultant solution with an organic solvent, washing the extract with aqueous alkali, drying the organic layer, evaporating to get crude Id, purifying the crude Id by chromatography to get pure Id as an yellow oil.

The said organic acid is acetic acid.

The said anhydride is acetic anhydride.

The said alkali is sodium bicarbonate.

The said organic solvent used for extraction is chloroform.

The invention further includes a process for preparing the chiral derivative of formula Ie wherein, comprising:

refluxing Ia with an appropriate alcohol and organic acid in toluene for 10–20 hours using Dean-Stark set up, washing the mixture with aqueous alkali solution, evaporating the organic phase, recrystallising from organic solvents or their appropriate mixtures yielding Ie as a solid.

The said appropriate alcohol is benzyl alcohol.

The said anhydride is acetic anhydride.

The said alkali is sodium bicarbonate.

The said organic solvent used for crystallization is selected from hexane or ether.

The invention further includes a process for preparing the chiral derivative of formula Ig comprising:

adding organic halide to a suspension of Ib in absolute alcohol, stirring the mixture for 24 hours, neutralizing the mixture with aqueous alkali solution, extracting the said mixture using organic solvent, evaporating the mixture furnishing Ig as a yellow oil.

The said organic halide is thionyl chloride.

The said alcohol is ethanol.

The said alkali is sodium bicarbonate.

The said organic solvent is chloroform.

The invention further includes a process for preparing the chiral derivative of formula Ih comprising:

adding an organic halide to a suspension of Ib in appropriate dry alcohol, stirring the mixture for 36 hours, neutralizing with aqueous alkali solution, extracting the said solution with an organic solvent.

evaporating and extracting using an appropriate organic solvent yielding Ih as a yellow oil.

The said organic halide is thionyl chloride.

The said appropriate alcohol is isopropyl alcohol.

The said appropriate alkali is sodium bicarbonate.

The said appropriate organic solvent is chloroform.

The organic solvent used after evaporation is hexane.

The invention further includes a process for preparing the chiral derivative of formulae Ij or Ik comprising:

refluxing the suspension of Ia in an organic halide for 3 hours, concentrating the said mixture under vacuum, dissolving the solid obtained in an organic solvent, adding an appropriate amine to the dissolved solution, stirring the mixture at room temperature for 4–18 hours concentrating the solution under vacuum, adding the organic halide to the semi-solid obtained refluxing for 18 hours, extracting with suitable organic solvent subjecting the said extract to chromatography furnishing Ij or Ik as white crystals.

The said organic halide is acetyl chloride.

The said appropriate amine is 4-methoxy benzyl amine.

The said organic solvent is chloroform.

The process will now be described with reference to the foregoing examples.

EXAMPLE 1

Hibiscus acid (Ia)

Ia is isolated from the leaves of *Hibiscus furcatus/ Hibiscus subdariffa* or from the calyxes of *Hibiscus sabdariffa* as given below (A and B).

A. Fresh leaves (1 kg) of *Hibiscus furcatus* was extracted with water (1 Lt). The concentrated aqueous extract was washed with hexane several times. To the aqueous layer, acetone (1 Lt) was added to precipitate insoluble materials. After evaporating the acetone, NaOH solution (8N, 80 ml) was added to adjust the pH to 12.0. Addition of alcohol (1 Lt) resulted in the precipitation of Na salt of Ia. The pH was re-adjusted to 2.0 by the addition of HCl (2N). The combined mixture was concentrated to a syrupy mass and extracted with dry acetone (2×250 ml). The acetone extract was concentrated. This was further extracted with ether (3×150 ml), followed by concentration yielded Ia (10 g) in the pure form.

B. Fresh calyxes (1 kg) of *Hibiscus sabdariffa* was extracted following the procedure described above (example IA) yielded Ia (16 g) in the pure form.

Melting point: 175° C. (decomp.)

EXAMPLE 2

Disodium (2S,3R)-tetrahydro-3-hydroxy-5-oxo-2,3-furandicarboxylate (Ib):

To an aqueous solution of Ia (1.0 g, 5 mmol, in 5 ml water), saturated sodium bicarbonate solution was added till the pH of the solution is neutral. The residue obtained after evaporation was washed with dry acetone (5×10 ml). The product Ib was finally dried under vacuum.

Yield: 1.0 g (82%).

EXAMPLE 3

(2S,3R)-Tetrahydro-3-hydroxy-5-oxo-2,3-furandicarbonylchloride (Ic)

To a suspension of Ib (1.0 g, 4.3 mmol) in ether (10 ml), thionyl chloride (1.0 ml, 14 mmol) was added. The mixture was stirred for two hours. The reaction mixture was filtered followed by evaporation gave Ic.

Yield: 0.6 g (62%).

EXAMPLE 4

Dimethyl (2S,3R)-tetrahydro-3-oxo-[(methylthio) methoxy]-5-oxo-2,3-furandicarboxylate (Id):

To a solution of If (5 g, 22.9 mmol) in DMSO (70 ml), acetic acid (6 ml) in acetic anhydride (50 ml) was added. The mixture was allowed to stand for three days. The reaction mixture was added to saturated aqueous solution of sodium bicarbonate (900 ml) and stirred for one hour. It was extracted with chloroform (3×350 ml) and the combined chloroform extracts was washed with saturated sodium bicarbonate solution (100 ml) followed by water (2×50 ml). The chloroform extract was dried (sodium sulphate) and evaporated to get crude Id (4 g). Id was further purified by column chromatography (silicagel 60–120 mesh, eluent: hexane-chloroform, 10–50%.

Yield: 2.5 g (38%)

EXAMPLE 5
Bis(phenylmethyl)(2S,3R)-tetrahydro-3-hydroxy-5-oxo-2,3 furandicarboxylate (Ie)

Ia (3.8 g, 20 mmol) was refluxed with benzyl alcohol (6.5 g, 60 mmol) and p-toluene sulphonic acid (50 mg, 0.25 mmol) in toluene (40 ml) for 13 hours using a Dean-Stark set up. The mixture was washed with aqueous sodium bicarbonate solution (50 ml). The aqueous phase was extracted using chloroform (20 ml). Evaporation of the combined extracts yielded Ie which was recrystallised from hexane-ether.

Melting point: 90° C. Yield: 3 g (4%)

EXAMPLE 6
Diethyl (2S,3R)-tetrahydro-3-hydroxy-5-oxo-2,3-furandicarboxylate (Ig):

To a precooled (−5–0° C.) suspension of Ib (1.0 g, 4.4 mmol) in dry ethanol (10 ml), thionyl chloride (0.7 ml, 10 mmol) was added. The mixture was then stirred for 24 hours at room temperature. After filtration of the reaction mixture, pH of the filtrate was adjusted to 7.0, by adding saturated aqueous solution of sodium bicarbonate and was extracted with chloroform (3×10 ml). The combined extract upon drying and evaporation furnished an oily residue of Ig.

Yield: 0.9 g (7%)

EXAMPLE 7
Diisopropyl (2S,3R)-tetrahydro-3-hydroxy-5-oxo-2,3-furandicarboxylate (Ih):

To a precooled (−5–0° C.) suspension of Ib (1.0 g, 4.4 mmol) in isopropyl alcohol (10 ml) and thionyl chloride (0.7 ml, 10 mmol) was added. The mixture was then stirred for 36 hours at room temperature. After filtration of the reaction mixture, pH of the filtrate was adjusted to 7.0, by adding saturated aqueous solution of sodium bicarbonate and was extracted with chloroform (3×10 ml). The organic layer was concentrated and extracted using hexane. The combined extract upon drying and evaporation furnished an oily residue of Ih.

Yield: 0.1 g (41%)

EXAMPLE 8
(3aR,6aS)-3a-(acetyloxy)dihydro-5-(4-methoxy-phenyl methyl)-6H-furo[2,3-c]pyrrole-2,4,6(3H,4H)-trione(Ij)

A suspension of Ia (1 g, 5 mmol) in acetyl chloride (4 ml) is refluxed for 3 hours followed by concentration under vacuum. The solid obtained is dissolved in THF (5 ml) and 4-methoxy benzyl amine (0.6 ml, 5 mmlol) is added. The mixture is stirred at room temparature for 18 hours followed by concentration under vacuum. To the semi-solid obtained acetyl chloride (5 ml) is added and the mixture is refluxed for 18 hours. Concentration under vacuum followed by column chromatography afforded Ij as white crystals. (Active neutral alumina, eluent: chloroform-hexane 50%)

Yield: 0.2 g (12%)

Advantages of the New Process:
1. Basically, the extraction is done with water. The use of undesirable solvent Methanol is totally replaced by water and use of solvent ether is reduced considerably. (Following the present method, for the isolation of 100 gms of hibiscus acid four liters of diethyl ether is used. However following the prior art fifty liters of ether is used in the second step for the isolation of 100 gms of the acid.)
2. The present method is general for fresh/dried leaves and calyxes of *Hibiscus sabdariffa*, leaves of *Hibiscus furcatus* and *Hibiscus cannabinus*. Process time is substantially reduced and the method is inexpencive. The leaves of the above plants are available through out South India in all seasons, in plenty.
3. The process is suitable for large-scale isolation and involves simple crystallisation techniques.
4. This process is a water process and which is entirely new from the method described in any of the prior arts.

USES:

Pharmaceutical applications

Chiral derivatives, Ia-Ik, are used as chiral synthons

REFERENCES

1. U.S. Pat. No. 4,005,086 dated Jan. 1, 1997
2. U.S. Pat. No. 4,006,166 dated Feb. 1, 1977
3. U.S. Pat. No. 4,007,208 dated Feb. 8, 1997
4. U.S. Pat. No. 5,536,516 dated Jul. 7, 1996
5. U.S. Pat. No. WO 9605741 A1 960229
6. U.S. Pat. No. WO 9636585 A1 961121
7. CA 86, 1977. 186629r.
8. CA 85, 1976, 41531x.
9. CA 87, 1977, 195626k.
10. CA 96, 1982, 30421n.
11. U.S. patent application Ser. No 09/365,300, 1999
12. Tetrahedron Letters Vol. 25 pp 4491–4494, 1984
13. Tetrahedron Vol. 43, No. 19, pp 4497–4506, 1987
14. Tetrahedron Vol. 38, No. 15, pp 2377–2394, 1982
15. Tetrahedron Vol. 34, pp 1449–1452, 1978
16. J. Org. Chem. 63, 2385–2388, 1998
17. J C S Chem. Comm pp 711, 1973
18. J. Org. Chem. 58, 2725–2737, 1993
19. Tetrahedron Vol. 31, pp 3011–3012, 1975
20. Tetrahedron Letters Vol. 22, No. 52, pp 5271–5274, 1981
21. Tetrahedron Letters Vol. 23, No. 48, pp 5051–5054, 1982
22. J. Org Chem. 1984, 49, 5041
23. Synthesis 89, 1986
24. J. Org. Chem. 1997, 62, 8560
25. Tetrahedron, Vol. 52. No. 7, pp 2603–2628, 1996
26. J. Org. Chem. 1993, 58, 2725
27. Tetrahedron Letters 1981, 22, 4611
28. J. Org Chem. 1984, 49, 2168 and references sited there in
29. Acta. Chem. Scand. 23, pp 286–293, 1969
30. Z. Physiol. Chem. 33, 1941, 269

We claim:

1. A chiral compound of Hibiscus acid bearing lactone moiety of formula I,

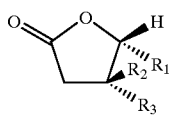

Wherein:

$R_1=R_2=$ (i) alkali salt of carboxylic acid or (ii) acid chloride or (iii) lower esters; and when $R_1$ is a lower ester, $R_2$ is an alkali of a carboxylic acid or an acid chloride and when $R_2$ is a lower ester, $R_1$ is an alkali salt of a carboxylic acid or an acid chloride and $R_3$ (i) hydroxyl or (ii) protected hydroxyl group.

2. A compound as claimed in claim 1 wherein, $R_1$ and $R_2$ is selected from —COONa, —COCl, —COOCH$_2$C$_6$H$_5$, —COOC$_2$H$_5$, —COOCH$_3$—, —COOCH(CH$_3$)$_2$; and $R_3$ is hydroxyl or a protected hydroxyl group.

3. A compound as claimed in claim 1 wherein, $R_1=R_2=$—COONa, $R_3=$—OH and said compound is Disodium (2S,3R)-tetrahydro-3-hydroxy-5-oxo-2,3-furandicarboxylate (Ib)

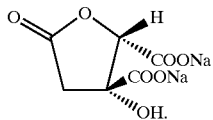

4. A compound as claimed in claim 1 wherein, $R_1=R_2=$—COCl, $R_3=$—OH and said compound is (2S,3R)-Tetrahydro-3-hydroxy-5-oxo-2,3-furandicarbonylchloride (Ic)

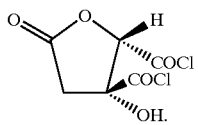

5. A compound as claimed in claim 1 wherein, $R_1=R_2=$COOCH$_3$, $R_3=$—OCH$_2$SCH$_3$ and said compound is Dimethyl(2S,3R)-tetrahydro-3-oxo -[(methylthio)methoxy]-5-oxo-2,3-furandicarboxylate (Id):

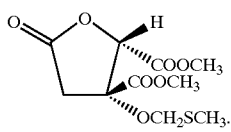

6. A compound as claimed in claim 1 wherein, $R_1=R_2=$COOCH(CH$_3$)$_2$, $R_3=$—OH and said compound is Diisopropyl (2S,3R)-tetrahydro-3-hydroxy -5-oxo-2,3-furandicarboxylate (Ih):

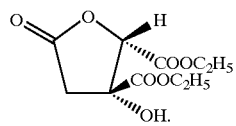

7. A process for the isolation of chiral molecule of formula Ia as claimed in claim 1 comprising:

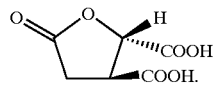

8. A process of preparing the chiral derivative of formula Ib as claimed in claim 3, comprising:

treating the aqueous solution of Ia with aqueous solution of alkali-till until the pH of the solution is neutral, evaporating the resultant solution to dryness washing the residue with water miscible organic solvent, drying the product 1b under vacuum.

9. A process of preparing the chiral derivative of formula Ic as claimed in claim 4, comprising:

adding an organic halide to a suspension of Ib in organic solvent, stirring the mixture for 14 hours, filtering the said mixture, evaporating the said solution to get Ic as a hygroscopic solid.

10. A process for preparing the chiral derivative of formula Id as claimed in claim 5, comprising:

adding DMSO, an organic acid and an anhydride to If, allowing the mixture to stand for 3–4 days, adding the reaction mixture to cold saturated aqueous solution of alkali, stirring the mixture for 1–4 hours, extracting the resultant solution with an organic solvent, washing the extract with aqueous alkali, drying the organic layer, evaporating to get crude Id, purifying the crude Id by chromatography to get pure Id as a yellow oil.

11. A process for preparing the chiral derivative of formula Ic, as claimed in claim 2 comprising:

refluxing Ia with an appropriate alcohol and organic acid in toluene for 10–20 hours using Dean-Stark set up, washing the mixture with aqueous alkali solution, evaporating the organic phase, recrystallising from organic solvents or their appropriate mixtures yielding Ic as a solid.

12. A process for preparing the chiral derivative of formula Ig, as claimed in claim 2, comprising:

adding organic halide to a suspension of Ib in absolute alcohol, stirring the mixture for 24 hours, neutralizing the mixture with aqueous alkali solution, extracting the said mixture using organic solvent, evaporating the mixture furnishing Ig as a yellow oil.

13. A process for preparing the chiral derivative of formula Ih, as claimed in claim 6 comprising:

adding an organic halide to a suspension of Ib in appropriate dry alcohol, stirring the mixture for 36 hours, neutralizing with aqueous alkali solution, extracting the said solution with an organic solvent, evaporating and extracting using an appropriate organic solvent yielding Ih as a yellow oil.

14. A process as claimed in claim 7 wherein, the organic solvent used for washing is hexane.

15. A process as claimed in claim 7 wherein, the organic solvent used for removing impurities is selected from methanol or acetone.

16. A process as claimed in claim 8 wherein, the said alkali is sodium bicarbonate.

17. A process as claimed in claim 10 wherein, the said alkali is sodium bicarbonate.

18. A process as claimed in claim 11 wherein, the said alkali is sodium bicarbonate.

19. A process as claimed in claim 12 wherein, the said alkali is sodium bicarbonate.

20. A process as claimed in claim 13 wherein, the said alkali is sodium bicarbonate.

21. A process, as claimed in claim 9 wherein, the said organic solvent is ether.

22. A process, as claimed in claim 12 wherein, the said organic halide is thionyl chloride.

23. A process, as claimed in claim 13 wherein, the said organic halide is thionyl chloride.

24. A process, as claimed in claim 10 wherein, the said organic acid is acetic acid.

25. A process, as claim 10 in claim wherein, the said anhydride is acetic anhydride.

26. A process, as claimed in claim 11 wherein, the said anhydride is acetic anhydride.

27. A process, as claimed in claim 10 wherein, the said organic solvent used for extraction is chloroform.

28. A process, as claimed in claim 12 wherein, the said organic solvent used for extraction is chloroform.

29. A process, as claimed in claim 11 wherein, the said appropriate alcohol is benzyl alcohol.

30. A process, as claimed in claim 11 wherein, the said organic solvent used for crystallization is selected from hexane or ether.

31. A process, as claimed in claim 12 wherein, the said alcohol is ethanol.

32. A process, as claimed in claim 13 wherein, the said appropriate alcohol is isopropyl alcohol.

33. A process, as claimed in claim 13 wherein, the organic solvent used after evaporation is hexane.

* * * * *